United States Patent [19]

Yoshimoto et al.

[11] Patent Number: 4,772,572
[45] Date of Patent: Sep. 20, 1988

[54] HYBRIDOMAS AND MONOCLONAL ANTIBODIES TO HUMAN IL-2

[75] Inventors: Ryota Yoshimoto; Yoshiaki Hanzawa, both of Kawasaki; Junji Hamuro, Yokohama, all of Japan

[73] Assignee: Ajinomoto Co., Inc., Tokyo, Japan

[21] Appl. No.: 838,209

[22] Filed: Mar. 10, 1986

Related U.S. Application Data

[63] Continuation of Ser. No. 525,721, Aug. 23, 1983, abandoned.

[30] Foreign Application Priority Data

Aug. 28, 1982 [JP] Japan .................................. 57-149753

[51] Int. Cl.$^4$ ..................... C12N 5/00; A61K 39/395; G01N 33/54; C12R 1/91
[52] U.S. Cl. ................................. 435/240.27; 435/68; 435/948; 436/548; 530/387
[58] Field of Search ....................... 435/68, 172.2, 240, 435/241, 948, 104, 108; 424/85; 436/548

[56] References Cited

U.S. PATENT DOCUMENTS

| 4,473,493 | 9/1984 | Gillis | 435/241 |
| 4,636,463 | 1/1987 | Altman et al. | 436/808 |
| 4,690,893 | 9/1987 | Mosmann | 435/68 |

OTHER PUBLICATIONS

Gillis et al., "Generation of a B Cell Hybridoma Whose Antibody Product Inhibits Interleukin 2 Activity", Journal of Immunology 126(5), pp. 1978-84 (1981).
Stadler et al., "Human Interleukin-2: Biological Studies Using Purified IL-2 and Monoclonal Anti-IL-2 Antiobodies", Lymphokines 6, pp. 117-35 (1982).
Stadler et al., "Monoclonal Antibody Against Human Interleukin 2 (IL 2), Journal of Immunology 128(4), pp. 1620-4 (4-1982).

*Primary Examiner*—John E. Tarcza
*Attorney, Agent, or Firm*—Oblon, Fisher, Spivak, McClelland & Maier

[57] ABSTRACT

Certain hybridomas preparing monoclonal antibodies to human interleukin-2 (IL-2) which do not cross react with rator mouse IL-2 are disclosed. The secreted monoclonal antibody can be used in immunoassays for human IL-2.

5 Claims, No Drawings

HYBRIDOMAS AND MONOCLONAL ANTIBODIES TO HUMAN IL-2

This application is a continuation of application Ser. No. 525,721, filed Aug. 23, 1983, now abandoned.

DETAILED EXPLANATION OF THE INVENTION

The present invention relates to a monoclonal antibody specific to human interleukin 2 (hereafter simply referred to as human IL2) induced from a hybridoma and a process for production thereof.

A hybridoma composed of a spleen cell and a myeloma cell is described in publications, e.g., see Koehler et al., *Nature*, 256, 495 (1975) and *Eur. J. Immunol.*, 6, 511 (1976); Milstein et al., *Nature*, 266, 550 (1977) and, Walsh, *Nature*, 266, 495 (1977). Prior to the present invention, however, nothing is known about a process for producing a monoclonal antibody to human IL2, that is, anti-human IL2 monoclonal antibody, by forming a hybridoma of an anti-human IL2 antibody-producing cell obtained by reacting human T lymphoma-induced IL2 as an antigen.

According to the present invention, a hybridoma clone which produces a and an anti-human IL2 monoclonal antibody having specificity to human IL2 monoclonal antibody having a homogeneous property, which is produced by the clone, are provided. Further, a method for quantitatively assaying a trace amount of IL2 as well as a method for purification using the monoclonal antibody are provided.

The hybridoma clone of the present invention is produced by forming a hybridoma from (a) a myeloma cell, that is, a malignant cell from an initial tumor of the marrow and (b) an antibody-producing cell present in the spleen or lymph node cells, cultivating and cloning this hybridoma and selecting as a clone which produces an antibody showing a specificity to human IL2.

The desired monoclonal antibody can be recovered from the culture supernatant obtained after culture of such a clone by purification procedures such as salting out, ion exchange chromatography, etc. If necessary, the whole culture supernatant can also be employed. Further, a monoclonal antibody, which is produced by transplating an anti-human IL2 antibody-producing hybridoma in the abdominal cavity of a histocompatible animal, a thymus-defective nude mouse, etc., growing there and accumulating in the ascite of the animal, can also be purified and recovered.

IL2 is a soluble immune-controlling substance which T lymphocyte produces. It is known that IL2 takes an important role as a controlling substance of an immune response through activation of various T cells, with the facts that (a) it proliferates a killer T lymphocyte or a helper T lymphocyte in vitro which has been functionally differentiated and matured; (b) it accelerates the cleavate of an immature thymocyte; (c) it induces a cytotoxic T lymphocyte from a thymocyte or a spleen cell of a nude mouse, in the presence of an antigen cell; (d) it induces an antibody-producing cell to a T cell-dependent antigen in a spleen cell of a T cell-deficient nude mouse to induce a helper T function; etc. Accordingly, measurement of a concentration of IL2 in blood from the patients with immunodeficiency disease, autoimmune diseases, cancers, etc. would be an extremely useful parameter for immunity to known any abnormality of the patients in immune functions.

By the provision of a monoclonal anti-human IL2 antibody in accordance with the present invention, the measurement of an IL2 content in blood which has been heretofore thought to be difficult due to the presence of the antibody in a trace amount in blood has become possible. That is, IL2 in blood can easily be quantitatively assayed through radioimmunoassay or enzymeimmunoassay using an anti-IL2 antibody.

Further, by binding the anti-human IL2 monoclonal antibody prepared in accordance with the present invention to an appropriate support such as a carrier resin or the like and performing affinity chromatography, a way that IL2 contained in a cell or in a medium in which a bacterium was cultured can be specifically purified to obtain a human IL2 having an extremely high purity has opened. For example, an anti-human IL2 monoclonal antibody can be bound to a support such as Sepharose (manufactured by Pharmacia Co., Ltd.) activated with cyanogen bromide, etc.; by performing affinity chromatography using a column prepared with this monoclonal antibody-bound support, IL2 can easily be purified. That is, after adsorbing IL2 specifically to the antibody column using a solvent having pH around neutral property, the column is thoroughly washed with the same solvent and the pH is reduced to about 2.8, or eluted with a solvent containing 1% sodium dodecyl sulfate (SDS) which keeps the pH around seven, thus the bound IL2 being eluted without the loss of its activity.

Further by performing radioimmunoassay or enzymeimmunoassay using the anti-human IL2 monoclonal antibody prepared in accordance with the present invention, a method for quantitatively assaying a trace amount of IL2 with high sensitivity is provided.

The hybridoma of the present invention is produced by fusing a myeloma cell and an antibody-producing cell. As antibody-producing cells, spleen or lymph node cells from animals such as mice, rats, etc. immunized with IL2, may be advantageously employed. The genus of an animal from which myeloma cells and antibody-producing cells are induced may be different from one another as long as both cells are fusible but, better results are generally obtained when cells of the same genus are employed.

A preferred hybridoma for practicing the present invention is a hybridoma between a spleen cell of a mouse immunized with human IL2 and a mouse myeloma cell. For example, excellent results were obtained with a hybridoma between an antibody-producing spleen cell of a BALB/C mouse previously immunized with a human T lymphoma-induced IL2 using as aluminum hydroxide and pertussis killed vaccine as adjuvant and a myeloma cell, P3-X63-Ag8-U1, of a BALB/C mouse. As myeloma cells, 8-azaguanine-resistant cell lines such as P3-X63-Ag8, P3-NSI/1-Ag4-1, MPC11-45.6.TG.1.7, SP2/V-Ag14 and X63-Ag8-6.5.3 (all from mouse), 210.RCY.Ag1.2.3 (rat), SKO-007 and GH15006TG-A12 (human), etc., in addition to P3-X63-Ag8-U1, are generally employed. Further antibody-producing cells may be advantageously obtained, for example, as follows. First, animals such as mice, rats, or the like are immunized with a human IL2. As human IL2 used herein, there are those induced from human tonsile lymphocytes, human peripheral blood lymphocytes, human lymphatic tumor cells such as human T lymphoma or artificial hybridomas. For reference, human T lymphoma-induced IL2 is superior to normal human lymphocyte-induced IL2 since it can easily be prepared in a large scale and an antigen having a high purity can be employed. Next, a spleen cell is prepared from an animal immunized. The method for the preparation thereof is well known in this technical field, but refer to, e.g., *Men-eki Jikken Sosaho*, A page 447 (edited by Nippon Men-eki Gakkai, 1975).

The preparation of a hybridoma and the selection of an anti-human IL2 antibody-producing clone can be carried out, for example, as follows. Antibody-producing cells are fused with myeloma cells using polyethylene glycol (PEG) or Sendai virus (HVC). The formed hybridomas are allowed to grow in a medium containing hypoxanthine, aminoputerine and thymidine. The antibody-producing cells and myeloma cells which were not fused are both dead in the medium and hybridomas alone are proliferated from respective clones. Clones which produce an anti-IL2 antibodies are selected from the grown hybridomas. All of the hybridomas do not always produce the antibodies. Antibodies produced from the respective clones vary in specificity and all of the clones do not always produce anti-human IL2 antibodies. Accordingly, clones which produces antibodies shown specificity to IL2 must be chosen.

The choice of anti-human IL2 antibody-producing clones can be carried out, for example, as follows. According to Gillis et al (*The Journal of Immunology (J. Immunol.*), vol. 120, page 2027 (1978)), cytotoxic T lymphocyte lines proliferate in the presence of IL2 and the uptake of radiation-marked tritiated thymidine into cells of CTLL increases in the presence of IL2 with an increase in DNA synthesis. CTLL also proliferate with human IL2 and this proliferative action is inhibited by an anti-human IL2 antibody. Thus, the presence or absence of anti-human IL2 antibody can be determined by determining whether or not the proliferation of CTLL is inhibited when the culture supernatant of hybridomas co-present with human IL2. If human IL2 antibody is specific to the active site of IL2, the activity of IL2 is inhibited by the addition of the antibody; in case that the specificity of the antibody is directed to the site other than the active site of IL2, the activity of IL2 disappears by precipitating an antigen-antibody complex by *Staphylococcus aureus* together with the antibody to absorb in and extinguish from the medium.

The hybridomas are consecutively subculturable in vitro over long periods of time and can be cultured in a flask, a dish, a roller bottle, a spinner flask, a rotary jar, a fermentation tank, etc. The hybridomas can also be allowed to grow in histocompatible animals or thymus-deficient nude mice. The hybridomas can be recovered from media or serum or ascites of animals, in a manner well known in the art. For example, refer to *Proceedings of the National Academy of Science, U.S.A. (Proc. Natl. Acd. Sci. U.S.A.)*, vol. 75, page 1510 (1978).

Hereafter, a typical example of processes for producing anti-human IL2 monoclonal antibodies through the preparation of a cell line of the hybridomas, is given below. The process given as an example indicates that spleen cells of BALB/C mice are fused with BALB/C-induced myeloma cells; however, the fusion can also be effected even using other antibody-producing cells and other myeloma cells. Similarly, in this process, human T cell leukemia cells J111 (ATCC CRL 8129)-induced human IL2 is employed in immunization but human IL2 induced from other cells can also be employed.

(a) Preparation of Antibody-Producing Spleen Cell:

BALB/C mice are immunized with 2,500 units of J111-induced human IL2 by intraperitoneally injecting together with 2 mg of aluminum hydroxide and $10^9$ pertussis killed vaccine. Fourteen days after, the mice are further supplementarily immunized with 5,000 units of IL2 by intramuscular injection at the five-divided portions in the back, together with 4 mg of aluminum hydroxide. Further 14 days after, the mice are supplementarily immunized with 5,000 units of IL2 by intraperitoneal injection without any adjuvant. The spleen is isolated 14 days after the final supplemental immunization and a cell suspension is prepared in accordance with the method of Gerhard et al (*Eur. J. Immunol.*, 5, 720 (1975)) and $5 \times 10^7$ cells are transferred into the vein of the BALB/C mice which was previously irradiated with x rays of 600 roentgens. Simultaneously, 10,000 units of IL2 are intraperitoneally injected together with 2 mg of aluminum hydroxide to effect supplemental immunization. Three days after, the spleen is isolated and a cell suspension is prepared, which is made antibody-producing cells for fusion.

(b) Preparation of Myeloma Cells:

Myeloma cells (P3-X63-Ag8-U1) from hypoxanthine phospholiposyl transferase-defficient BALB/C mice as described in *Proceedings of the National Academy of Science U.S.A. (Proc. Natl. Acad. Sci. U.S.A.)*, 76, 4061 (1979) are maintained in a medium, for example, an RPMI-1640 medium containing 10% fetal calf serum (FCS). The growth of P3-X63-Ag8U1 is inhibited by a hypoxanthine.aminopurarine.thymidine medium (HAT medium).

(c) Preparation of Hybridoma:

Spleen cells and myeloma cells are allowed to fuse in the presence of polyethylene glycol (PEG) 1,000, in accordance with the method of Koprowski et al (*Proc. Natl. Acd. Sci. U.S.A.*, 74, 2985 (1977)). After completion of the fusion treatment, the cells are suspended in a HAT medium described in *Science*, vol. 145, page 709 (1964) by Littlefield and the suspension is inoculated in each of wells of a tissue culture plate. In this case, it is preferred that a small quantity of thymocytes of BALB/C mice be co-present as nutrient cells. One, two and three days after the initiation of the culture, the half of the HAT medium in each of the wells is replaced with a fresh HAT medium and the half of a medium containing hypoxanthine.thymidine alone (HT medium) is replaced with fresh one further 14, 15 and 16 days after.

(d) Inspection of Anti-Human IL2 Antibody-Producing Hybridoma:

The hybridomas grown in the HAT medium is transferred to an ordinary medium, for example, an RPM1-1640 medium containing 10% FCS and the culture supernatant is employed as a standard specimen of anti-human IL2 antibody as it is. CTLL is suspended in, e.g., a Click's medium containing 2% FCS. Human IL2, the standard specimen, CTLL and the Click's medium are added to each of wells of a tissue culture microplate to fill up. In case that it is wished to precipitate the antigen-antibody complex, killed vaccine of *Staphylococcus aureus* is added to the medium, instead of the medium. After culturing for 24 hours, radiation-marked thymidine with tritium is added and the mixture is cultured for further 4 hours. Then, it is examined by radiation activity incorporated into the cells whether or not an increase of thymidine which CTLL incorporates by human IL2 is inhibited by the anti-human IL2 antibody standard specimen. The measurement of the radiation activity can easily be carried out in accordance with a method well known in the art.

(e) Cloning Selection of Hybridomas:

The hybridomas which were recognized to be antibody-active by the procedure of (d) are further cloned by the limiting dilution method well known in the art. The antibody activity of the culture supernatant of the grown clones is further inspected by the method of (d) to select clones having strong antibody activity.

(f) Preparation of Anti-human IL2 Monoclonal Antibodies:

To prepare anti-human IL2 monoclonal antibodies using the selected clones, the following procedure is carried out. That is, the clones are cultured in an appropriate medium, for example an RPMI-1640 medium containing 10% FCS until the cell concentration reaches the upper limit. After the culture, the cells are removed from the culture solution by centrifugal operation. Antibodies are contained in the culture solution.

(g) Purification of Anti-human IL2 Monoclonal Antibodies:

The purification of the monoclonal antibodies from the culture supernatant or the ascites can easily be carried out using methods well known in the art.

(h) Human IL2 Specific Assay System:

The anti IL2 antibody purified by the methods mentioned under (g) is first fixed onto a microplate well. Next, after application of an IL-2 sample to be tested on the well, followed by addition of biotinated-anti IL-2 antibody, and the antibody binds to IL-2 depending on the amount of it. Moreover, avidin-conjugated enzyme (e.g., avidin-conjugated alkaline-phosphatase (E. Y. Laboratory Inc., U.S.A)) is reacted with the antibody-IL2 complex which has been already accomplished on the well. The enzyme bound to antibody by the specific binding of avidin and biotin reacts with an appropriate substrate (e.g., p-nitrophenyl phosphate) to be colored. The IL2 assay system being able to measure a small amount of IL2 reading the value of absorbance (or optical density) has been establised.

The examples below are to exemplify the present invention but are not deemed to limit the scope of the present invention.

EXAMPLE 1

(Preparation of Anti-Human IL2 Antibody-Producing Hybridoma)

2,500 Units of IL2 obtained by stimulating human T cell leukemia cells J-111 (ATCC CRL 8129) with concanavalin A were intraperitoneally injected to BALB/C mice, together with 2 mg of aluminum hydroxide and $10^9$ cells of pertussis killed vaccine to cause immunization. Fourteen days after, 5,000 units of IL2 were further intramuscularly injected at the five portions of the back together with 4 mg of aluminum hydroxide to cause supplemental immunization. Further 14 days after, 5,000 units of IL2 were intraperitoneally injected without using any adjuvant to cause supplemental immunization. The spleen cells were isolated 14 days after the final supplemental immunization and 1 ml of the suspension obtained by supspending the cells using a Dulbecco-modified Eagle's medium (DMEM) so as to contain $5 \times 10^7$ cells was transfused into the vein of BALB/C mice which had been previously irradiated with x rays of 600 roentgens. Simultaneously, 10,000 units of IL2 were intraperitoneally injected together with 2 mg of aluminum hydroxide to cause supplemental immunization.

The spleen cells were isolated 3 days after and a cell suspension was prepared using DMEM and, 10 ml of DMEM containing $10^7$ spleen cells was mixed with $2 \times 10^6$ P3-X63-Ag8-U1 myeloma cells which were previously suspended in 10 ml of DMEM. The mixture was centrifugated at 800 g for 5 minutes. After removing the supernatant, the container was well shaken and the precipitated cells were loosened. Thereafter, 250 µl of DMEM containing 50% polyethylene glycol (PEG) 1000 (manufactured by Wako Junyaku Co., Ltd.) was added and the mixture was mildly agitated. After the addition of PEG, 0.5 ml of DMEM was continued to add every 1 minute to make the total contact 2.25 ml. Further 1 minute after, 10 ml of DMEM was added and then centrifugation was performed at 500 g for 5 minutes. After removing the supernatant, the cells were suspended in an RPMI-1640 medium containing 10% fetal calf serum and the suspension was inoculated by 200 µl each in each of wells of a tissue culture plate (96 wells, manufactured by Kostar Co., Ltd.). Cultivation was carried out at 37° C. in the presence of 5% $CO_2$. The half (100 µl) of the medium was replaced with an HAT medium (RPMI-1640 medium to which 10% fetal calf serum, $4 \times 10^{-7}$M aminopuҭerine, $1.6 \times 10^{-5}$M thymidine and $1 \times 10^{-4}$M hypoxantine were added) 1, 2, 3 and 7 days after to further continue the culture. The half (100 µl) of the medium was replaced by an HT medium (RPMI-1640 medium to which 10% fetal calf serum, $1.6 \times 10^{-5}$M thymidine and $1 \times 10^{-4}$M hypoxantine were added) 11, 13 and 14 days after.

16 Days after the initiation of the fusion operation, colonies of hybridomas appeared in 14 wells. The hybridomas were cultured in an RPMI-1640 medium containing 10% FCS and, the anti-IL2 activity of the culture supernatant was measured as follows.

The culture supernatant was used as a specimen solution and, 50 µl of the specimen solution, 50 µl of J111-induced human IL2 and further $4 \times 10^3$ cells of CTLL in the total amount of 200 µl were mixed with a Click/RPMI medium. The mixture was inoculated in each of wells of a tissue culture plate (96 wells, manufactured by Kostar Co., Ltd.). After culturing for 24 hours, labelling with 0.5 µCi of tritiated thymidine (NET-027X, manufactured by New England Nuclear Co., Ltd.) in each of the wells was carried out for last 4 hours. The cells were harvested on a glass filter using a harvester for microplate and, it was examined whether or not the proliferation of CTLL by the harvested IL2 was inhibited by the hybridoma culture supernatant.

As shown in Table 1, it is understood from the amount of tritiated thymidine 3H-TdR incorporated that the hybridoma named H-3 inhibited the proliferation of CTLL.

TABLE 1

| Cell Line | Incorporation of 3H—TdR ($\times 10^4$ cpm) |
|---|---|
| RPMI-1640 medium (blank) | 2.6 |
| P3-X63-Ag8-U1 | 3.2 |
| hybridoma H-1 | 1.8 |
| hybridoma H-2 | 1.9 |
| hybridoma H-3 | 0.92 |
| hybridoma H-4 | 3.0 |
| hybridoma H-5 | 2.8 |
| hybridoma H-6 | 3.3 |
| hybridoma H-7 | 2.2 |
| hybridoma H-8 | 2.76 |
| hybridoma H-9 | 2.96 |

TABLE 1-continued

| Cell Line | Incorporation of 3H—TdR ($\times 10^4$ cpm) |
|---|---|
| hybridoma H-10 | 3.36 |
| hybridoma H-11 | 2.42 |
| hybridoma H-12 | 3.18 |
| hybridoma H-13 | 3.1 |
| hybridoma H-14 | 1.96 |

EXAMPLE 2

(Cloning of Anti-Human IL2 Antibody-Producing Cell Line)

The hybridoma H-3 cell line was suspended in an RPMI-1640 medium containing 10% FCS in a concentration of 1 cell/ml. The suspension was inoculated in a tissue culture plate (96 wells, manufactured by Kostar Co., Ltd.) so as to be 200 μl in each of the wells and cloning was carried out by the limiting dilution method. 14 Days after, 48 hybrodoma clones appeared in 480 wells.

The results obtained by measuring anti-IL2 activity of the supernatant of each of the clones in accordance with Example 1 are shown in Table 2. Some clones showed anti-human IL2 activity; H-3-12 showed particularly strong anti-human IL2 activity.

TABLE 2

| Clone | Incorporation of 3H—TdR ($\times 10^4$ cpm) |
|---|---|
| RPMI-1640 medium (blank) | |
| H-3 | 1.04 |
| H-3-1 | 1.3 |
| H-3-10 | 0.94 |
| H-3-12 | 0.4 |
| H-3-18 | 1.4 |
| H-3-20 | 0.9 |
| H-3-25 | 2.2 |
| H-3-27 | 2.7 |
| H-3-32 | 1.6 |
| H-3-38 | 0.9 |
| H-3-40 | 0.8 |
| H-3-41 | 1.3 |
| H-3-45 | 1.1 |
| H-3-47 | 2.2 |
| H-3-48 | 1.8 |

EXAMPLE 3

(Production of Anti-Human IL2 Antibody)

The supernatant of the hybridoma H-3-12 clone was incubated at 37° C. minutes together with Staphylococcal bacteria Igsorb manufactured by The Enzyme Center. After absorbing IgG thereto, centrifugation was carried out at 3,000 g for 10 minutes and anti-human IL2 activity of the supernatant was measured in a manner similar to Example 1.

As shown in Table 3, it is understood that anti-human IL2 activity disappeared in the supernatant to which IgG was absorbed with Igsorb and the H-3-12 clone produced anti-human IL2 IgG antibody.

TABLE 3

| Sample | Incorporation of 3H—TdR ($\times 10^4$ cpm) |
|---|---|
| RPMI-1640 medium (blank) | 1.8 |
| H-3-12 | 0.3 |
| H-3-12 (treated with Igsorb) | 1.6 |

EXAMPLE 4

(Separation and Purification of Anti-Human IL2 IgG Antibody)

The culture supernatant of the H-3-12 clone was subjected to salting out with 35% saturated ammonium sulfate. After dissolving the resulting precipitates in the minimum amount of a 50 mM tris-hydrochloride buffer solution, ion exchange chromatography was carried out using DEAE-Cellulose (manufactured by Pharmacia Co., Ltd.) which had been previously equilibrated with a similar buffer solution and, anti-human IL2 activity of the IgG fraction eluted in the non-adsorbed fractions was measured in a manner similar to Example 1.

Table 4 shows the results. By doing so, anti-human IL2 IgG antibody can be separated and purified.

TABLE 4

| Sample | Incorporation of 3H—TdR ($\times 10^4$ cpm) |
|---|---|
| RPMI-1640 medium (blank) | 1.92 |
| H-3-12 | 0.26 |
| H-3-12 IgG Fraction | 0.4 |

EXAMPLE 5

(Specific Separation and Purification of IL2)

The anti-human IL2 IgG antibody separated and purified in Example 4 was bound to Sepharose (manufactured by Pharmacia Co., Ltd.) activated with cyanogen bromide to prepared anti-human IL2 IgG bound-Sepharose gel. The supernatant stimulated with human T cell line leukemia cells J-111 (ATCC CRL 8129) with Con A was passed trhough a column prepared using the gel to bind IL2 contained in the supernatant to the anti-IL2-IgG bound Sepharose.

After washing the column with a sufficient amount of a phosphate buffer solution (20 mM, pH 7.2), IL2 was eluted with a 0.1M glycine-hydrochloride buffer solution (pH 7.2). After dialyzing the eluted solution with a 20 mM phosphate buffer solution (pH 7.2) containing 0.9% NaCl, IL2 activity was examined through DNA synthesis of CTLL cells.

Otherwise, after washing the column with a phosphate buffer solution, IL2 was eluted with a 1% sodium dodecyl sulfate (SDS) (79° C.). Soon after the elution procedure, the eluted solution was kept on ice to precipitate and eliminate free SDS in it. The IL-2 activity was examined as mentioned above.

As shown in Table 5, it is understood that IL2 was recovered in the fraction showing affinity to anti-IL2-IgG Sepharose to which it is bound.

TABLE 5

| Sample | Incorporation of 3H—TdR ($\times 10^4$ cpm) |
|---|---|
| RPMI-1640 medium | 0.22 |
| ATCC CRL 8129 IL2 | 1.8 |
| IgG Sepharose-non-Absrobed Fraction | 0.3 |
| IgG Sepharose-Adsorbed Fraction (eluted at pH 2.8) | 2.4 |
| IgG Sepharose-Adsorbed Fraction (eluted with 1% SDS) | 2.6 |

EXAMPLE 6

(Preparation of Anti-Human IL2 IgM Antibody-Producing Hybridomas)

Anti-IL2 antibody-producing hybridomas were prepared in a manner similar to Example 1. Anti-IL2 activity of the culture supernatant of the thus obtained hybridoma colony was examined in a manner similar to Example 1.

As shown in Table 6, the results indicate that anti-IL2 activity was noted in hybridomas named A 70.

TABLE 6

| Cell Line | Incorporation of 3H—TdR ($\times 10^4$ cpm) |
| --- | --- |
| RPMI-1640 medium | 1.4 |
| P3-X63-Ag8-U1 hybridoma | 2.3 |
| A56 | 1.5 |
| A60 | 2.0 |
| A64 | 1.6 |
| A65 | 1.5 |
| A66 | 1.8 |
| A68 | 1.8 |
| A70 | 0.5 |
| A71 | 2.0 |
| A72 | 1.9 |
| A77 | 1.7 |
| A78 | 1.7 |
| A80 | 1.8 |
| A82 | 1.7 |
| A83 | 1.9 |

Next, goat IgG antibody (manufactured by Capelle Laboratories, Co., Ltd.) to mouse IgM was added to the culture supernatant of A 70. After incubating at 37° C. for 1 hour, Igsorb was added and the mixture was further incubated at 37° C. for 30 minutes. Igsorb was precipitated by centrifugal operation and anti-IL2 activity of the supernatant was examined in a manner similar to Example 1.

As a result, as shown in Table 7, anti-IL2 activity of the A 70 hybridomas disappeared by the IgM absorption operation and it is thus understood that anti-IL2 antibody produced by A 70 was IgM.

TABLE 7

| Treatment of A 70 Culture Supernatant | Incorporation of 3H—TdR ($\times 10^4$/ml) |
| --- | --- |
| no treatment | 0.7 |
| absorbed with Igsorb | 0.5 |
| absorbed with Igsorb and anti-IgM antibody | 1.8 |
| RPMI-1640 medium (control) | 2.0 |

EXAMPLE 7

(Transplantation of Anti-IL2 Antibody-Producing hybridomas in the Abdominal Cavity of Mouse)

A suspension of $5 \times 10^6$ cells of hybridomas H 3 in 0.5 ml of a physiological saline solution were transplanted in the abdominal cavity of BALB/C mouse. After confirming that the abdomen of the mouse was enlarged, the proliferated cells were recovered with a syringe 10 days after. The cells were removed from the ascites by centrifugal operation and, anti-IL2 activity was examined in a manner similar to Example 1.

Table 8 shows the results and it is understood that anti-IL2 antibody was produced from H3 in the ascites.

TABLE 8

| Sample | Incorporation of 3H—TdR ($\times 10^4$ cpm) |
| --- | --- |
| P3-X63-Ag8-U1 Ascites of Transplanted Mouse | 2.8 |
| Ascite of H3 Transplanted Mouse | 0.2 |
| Ascites of Intact Mouse | 2.3 |

EXAMPLE 8

(Specific Detection and Quantitative Determination of IL2)

Purified anti-human IL2 IgG antibody obtained in Example 4 was diluted with Phosphate Buffered Saline (PBS) to 100 μg/ml. The diluent was distributed in an amount of 40 μl into each well of a 96-welled microplate, and incubated for 1 hour at room temperature to be fixed.

After washing the wells with RIA buffer (PBS+0.5% BcVine Serum albumin) three times, human IL-2 was applied on the wells (20 μl/well), incubated for 1 hour at room temp. and washed with the same procedure as mentioned above.

Purified biotinated-anti-2 IgG antibody (30 μg/well) was reacted in the wells for 1 hour at room temperature followed by another washing. After application of avidin-conjugated enzyme, followed by washing out of free enzyme, a substrate was added to be colored.

At the point when appropriate color condition appeared, 3M NaOH was added to stop the reaction and the value of absorbance was measured.

TABLE 9

| IL2 Dilution (x) | $OD_{405}$ IL2 (1,000 u/ml) | BSA (100 μg/ml) |
| --- | --- | --- |
| 2 | 1.45 | 0.1 |
| 4 | 1.35 | 0.05 |
| 8 | 1.0 | 0.05 |
| 16 | 0.5 | 0.1 |
| 32 | 0.3 | 0.05 |
| 64 | 0.3 | 0.2 |
| 128 | 0.25 | 0.05 |
| 256 | 0.2 | 0.1 |

Cultures of the cell lines identified below were deposited with and are available from the Institute for Fermentation, Osaka, which is located at 17-85, Josu-Honmachi 2-chome, Yodogawa-Ku, Osaka 532:

| Cell line as identified in specification | IFO |
| --- | --- |
| H-3-12 | IFO 50083 |
| A-70 | IFO 50084 |

What is claimed is:

1. In a method for quantitatively assaying a trace amount of human interleukin 2, an improvement which comprises:
    conducting said assay with anti-human interleukin 2 monoclonal antibody, wherein said antibody is selected from antibodies produced by cell lines H-3-12 and A-70.
2. A hybridoma cell line having the identifying characteristics of H-3-12.
3. A hybridoma cell line having the identifying characteristics of A-70.
4. A monoclonal antibody produced by a hybridoma cell line having the identifying characteristics of H-3-12.
5. A monoclonal antibody produced by a hybridoma cell line having the identifying characteristics of A-70.

* * * * *